United States Patent [19]

Moore

[11] 4,012,436

[45] Mar. 15, 1977

[54] CARBAMOYL CHLORIDES

[75] Inventor: Joseph E. Moore, Richmond, Calif.

[73] Assignee: Chevron Research Company, San Francisco, Calif.

[22] Filed: Feb. 12, 1975

[21] Appl. No.: 549,215

Related U.S. Application Data

[63] Continuation-in-part of Ser. No. 317,311, Dec. 21, 1972, abandoned.

[52] U.S. Cl. .............................. 260/481 R; 71/98; 260/346.2 R; 260/544 C; 260/553 A; 260/553 C

[51] Int. Cl.² ...................................... C07C 161/00

[58] Field of Search ..................... 260/544 C, 481 R

[56] References Cited

UNITED STATES PATENTS

| | | | |
|---|---|---|---|
| 3,625,970 | 12/1971 | Ambrus | 260/544 C |
| 3,625,993 | 12/1971 | Horn | 260/544 C |
| 3,639,471 | 2/1972 | Klauke et al. | 260/544 C |
| 3,699,163 | 10/1972 | Kohn | 260/544 C |
| 3,711,530 | 1/1973 | Kobzina | 260/544 C |

FOREIGN PATENTS OR APPLICATIONS

| | | | |
|---|---|---|---|
| 772,634 | 9/1971 | Belgium | 260/544 C |

OTHER PUBLICATIONS

Haas, Chem. Abstracts 64:15723d–g.

*Primary Examiner*—Vivian Garner
*Attorney, Agent, or Firm*—G. F. Magdeburger; Dix A. Newell; Raymond Owyang

[57] ABSTRACT

N-substituted-thio N-alkyl carbamoyl chlorides are prepared by reacting an N-arylthio- or N-aliphaticthio-N-alkylamine with phosgene. The N-arylthio- or N-aliphaticthio-N-alkyl carbamoyl chlorides are useful intermediates for the preparation of pesticides.

2 Claims, No Drawings

CARBAMOYL CHLORIDES

CROSS-REFERENCE TO RELATED APPLICATION

This application is a continuation-in-part of U.S. Ser. No. 317,311, filed Dec. 21, 1972, now abandoned.

BACKGROUND OF THE INVENTION

U.S. Pat. No. 3,639,471, issued Feb. 1, 1972, to E. Klauke and E. Kuhle, discloses the preparation of N-arylthio and N-aliphaticthio carbamoyl fluorides by the reaction of a carbamoyl fluoride and a sulfenyl chloride. However, as disclosed in U.S. Pat. No. 3,639,471, the process of Klauke and Kuhle is not suitable for preparing the corresponding carbamoyl chlorides. Since fluorine-containing compounds are generally more expensive than the corresponding chlorine-containing compounds, it would be advantageous to develop a process for the preparation of N-arylthio and N-aliphaticthio carbamoyl chlorides.

SUMMARY OF THE INVENTION

It has now been found that N-arylthio and N-aliphatic-thio-N-alkyl carbamoyl chlorides are prepared in good yields by the reaction of a sulfenylated monoalkylamine and phosgene.

DESCRIPTION OF THE INVENTION

The sulfenylated amine reactant employed in the process of the invention is represented by the formula (I):

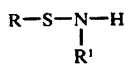
(I)

wherein R is alkyl of 1 to 6 carbon atoms, alkyl of 1 to 6 carbon atoms, and of 1 carboalkoxy group of 2 to 6 carbon atoms, haloalkyl of 1 to 6 carbon atoms and of 1 to 5 fluorine, chlorine or bromine atoms, haloalkyl of 1 to 6 carbon atoms, of 1 to 5 fluorine, chlorine or bromine atoms and of 1carboalkoxy group of 2 to 6 carbon atoms, or pheyl substituted with up to 2 (0 to 2) fluorine, chlorine or bromine atoms, alkyl of 1 to 4 carbon atoms, alkoxy of 1 to 4 carbon atoms or nitro: and $R^1$ is alkyl of 1 to 6 carbon atoms.

Illustrative alkyl groups which R and $R^1$ may represent include methyl, ethyl, n-propyl, isopropyl, n-butyl, t-butyl, sec-pentyl, n-hexyl, etc.

Illustrative carboalkoxy-substituted alkyl R groups include carbomethoxymethyl, 2-carbethoxyethyl, etc.

Illustrative haloalkyl R groups include chloromethyl, bromomethyl, dichloromethyl, dibromomethyl, trifluoromethyl, fluorodichloromethyl, trichloromethyl, tribromomethyl, 2-chloroethyl, 2,2-difluoroethyl, 1,1,2,2-tetrachloroethyl, 1,2,2,2-tetrachloroethyl, pentachloroethyl, 3-fluoropropyl, 4-chlorobutyl, 2,4,6-trichlorohexyl, 3,5-dichloropentyl, etc.

Illustrative carboalkoxy-substituted haloalkyl R groups include carbomethoxydichloromethyl, 4-carbobutoxy-2,2-dichlorobutyl, etc.

Illustrative aryl R groups include phenyl, 2-methylphenyl, 4-methoxyphenyl, 2,4-dimethylphenyl, 4-ethylphenyl, 4-isopropylphenyl, 4-nitrophenyl, 2-fluorophenyl, 4-chlorophenyl, 4-bromophenyl, 2,4-dichlorophenyl, 3,4-dichlorophenyl, and 2-chloro-4-methylphenyl.

Preferred R groups are haloalkyl of 1 to 3 carbon atoms and 1 to 5 chlorine or bromine atoms, and haloalkyl of 1 to 3 carbon atoms, of 1 to 5 chlorine or bromine atoms, and of 1 carboalkoxy of 2 to 6 carbon atoms. Particularly preferred R groups are chloromethyl and chloroethyl of 1 to 5 chloroine groups.

Preferred $R^1$ groups are lower alkyl of 1 to 3 carbon atoms, especially methyl or ethyl.

The amine reactant (I) is prepared by the reaction of an amine of the formula (II)

II.

and a sulfenyl halide of the formula

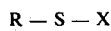
III.

wherein R and $R^1$ have the same significance as defined above and X is chlorine or bromine. The reaction is generally carried out in an organic solvent such as acetonitrile, dimethylformamide, etc. The quantity of solvent employed varies from about 2 to 10 times the volume of the reactants. The molar ratios of the sulfenyl halide (III) to the amine (II) is generally about 2:1 to 1:2, although molar ratios of about 1.2:1 to 1:1.2 are preferred. An acid acceptor, e.g., a soluble organic base, is used in amounts ranging from about 1 to 2 mols per mol of the sulfenyl halide to scavenge the hydrogen chloride by-product.

The preferred organic bases are organic amines such as trialkyl amines of 3 to 10 carbon atoms, e.g., trimethylamine, and pyridine and alkylpyridine of 6 to 10 carbon atoms, e.g., lutidine.

The reaction is conducted at temperatures ranging from about 0° to 50° C, preferably 0° to 25° C. The reactants are mixed, for example, by slowly adding the sulfenyl halide (III) to the amine (II) and the organic base in a solvent, and allowed to react at these temperature ranges for about ½ to 5 hours. The reaction is preferably carried out at atmospheric pressure.

The amine product (I) is isolated by adding a water-insoluble organic solvent such as benzene, toluene, chloroform or ether to the reaction mixture, followed by sufficient water to form two layers. After separation, the aqueous layer is extracted with the organic solvent. The combined organic layers are dried and the solvent removed by distillation to give the crude product, which may be used as such or purified before use by chromatography, crystallization, or the like. In a preferred modification of the process, the sulfenylated amine product mixture from the reaction of the amine (II) and the sulfenyl halide (III) is employed directly for further reaction with phosgene without purification. In another preferred modification, the sulfenylated amine product mixture is filtered to remove amine hydrochloride salts formed from the hydrogen chloride by-product and the organic amine acceptor and then used without additional purification for further reaction with phosgene.

REACTION CONDITIONS

The sulfenylated amine reactant (I) is contacted with phosgene in the liquid phase in the presence of inert reaction solvent or diluent which is liquid at reaction temperature and pressure. Illustrative organic solvents are aromatic compounds such as benzene, toluene, chlorobenzene; alkanes such as heptane and isooctane; cycloalkanes such as cyclohexane; and haloalkanes such as methylene chloride. Other suitable organic solvents include nitriles such as acetonitrile and propionitrile; and dialkylamides such as dimethylformamide. The amount of organic solvent employed is generally from about 1 to 10 mols per mol of the sulfenylated amine reactant.

The molar ratio of the sulfenylated amine reactant (I) and phosgene is generally about 2:1 to about 1:5, although molar ratios of about 1:1 to 1:2 are preferred.

The reaction of the sulfenylated amine (I) and phosgene produces hydrogen chloride as a by-product. In one modification of the reaction, an acid acceptor is employed to complex the hydrogen chloride. Suitable acid acceptors include organic amines free of amino hydrogens, i.e., —N—H groups, such as organic tertiary amines and pyridine compounds. Illustrative organic tertiary amines include trialkylamines such as triethylamine, tripropylamine, N-methylpiperidine, etc., and illustrative pyridine compounds include pyridine, 2-methylpyridine, 3-methylpyridine, etc.

The precise method of contacting the sulfenylated amine (I) and the phosgene reactant is not critical. In one modification, the sulfenylated amine, solvent and acid acceptor are charged to a reactor and phosgene is introduced continuously to the reactor while the reaction mixture is maintained with agitation at reaction temperature and pressure. In another modification, phosgene is introduced into a reactor containing the crude amine product mixture resulting from the reaction of the amine (II) and the sulfenyl halide (III). By any modification, the process is conducted at moderate temperature and pressure. Suitable reaction temperatures vary from about 0° C to 60° C, but preferably from 0° C to 25° C. The reaction is conducted at or about atmospheric pressure. Typical pressures vary from about 1 to 10 atmospheres.

The carbamoyl chloride product is separated and recovered from the reaction mixture by conventional methods such as selective extraction, filtration, chromatography, and the like. The reaction solvent and any unreacted reactants are recycled for further utilization.

The Carbamoyl Chloride Product

The carbamoyl chloride produced by the process of the invention is represented by the formula (IV):

$$R-S-N-\overset{\overset{O}{\|}}{C}-Cl \quad (IV)$$
$$\phantom{R-S-N}|\phantom{C-Cl}$$
$$\phantom{R-S-N}R^1$$

wherein R and R¹ have the same significance as previously defined.

Illustrative carbamoyl chlorides include:
N-methylthio-N-methylcarbamoyl chloride,
N-ethylthio-N-methylcarbamoyl chloride,
N-propylthio-N-methylcarbamoyl chloride,
N-butylthio-N-methylcarbamoyl chloride,
N-hexylthio-N-hexylcarbamoyl chloride,
N-fluoromethylthio-N-methylcarbamoyl chloride,
N-carbomethoxymethylthio-N-methylcarbamoyl chloride,
N-carbomethoxydibromomethylthio-N-methylcarbamoyl chloride,
N-difluoromethylthio-N-methylcarbamoyl chloride,
N-trifluoromethylthio-N-methylcarbamoyl chloride,
N-trichloromethylthio-N-methylcarbamoyl chloride,
N-trichloromethylthio-N-ethylcarbamoyl chloride,
N-tribromomethylthio-N-methylcarbamoyl chloride,
N-fluorodichloromethylthio-N-ethylcarbamoyl chloride,
N-1,1,2,2-tetrachloroethylthio-N-methylcarbamoyl chloride,
N-1,2,2,2-tetrachloroethylthio-N-methylcarbamoyl chloride,
N-pentachloroethylthio-N-methylcarbamoyl chloride,
N-5-chloropentylthio-N-methylcarbamoyl chloride,
N-penylthio-N-methylcarbamoyl chloride,
N-p-tolythio-N-methylcarbamoyl chloride,
N-3-nitrophenylthio-N-hexylcarbamoyl chloride,
N-3-chloro-4-methylphenylthio-N-ethylcarbamoyl chloride, and
N-4-bromophenylthio-N-methylcarbamoyl chloride.

The carbamoyl chlorides are useful intermediates for the preparation of pesticides. For example, the carbamoyl chlorides can be reacted with benzofuranols to produce insecticidal N-thio-substituted benzofuranyl carbamates. Also, the carbamoyl chlorides can be reacted with amines to produce herbicidal N-thio-substituted ureas.

A preferred class of herbicidal ureas is prepared by the following reaction (1)

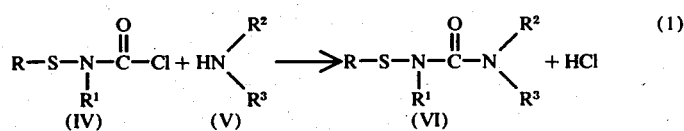

wherein R and R¹ are as defined above, R² is hydrogen or alkyl of 1 to 6 carbon atoms and R³ is phenyl substituted with up to 2 (0 to 2) fluorine, chlorine or bromine atoms, trifluoromethyl, trichloromethyl, alkyl of 1 to 4 carbon atoms, akoxy of 1 to 4 carbon atoms, and nitro.

The preferred ureas of Formula (VI) are those wherein R is alkyl of 1 to 6 carbon atoms and of 1 carboalkoxy of 2 to 6 carbon atoms or haloalkyl of 1 to 6 carbon atoms, of 1 to 5 fluorine, chlorine or bromine atoms and of 1 carboalkoxy of 2 to 6 carbon atoms. The most preferred ureas are those wherein R is haloalkyl of 1 to 3 carbon atoms, of 1 to 5 chlorine or bromine atoms and of 1 carboalkoxy of 2 to 6 carbon atoms.

Reaction (1) is conducted by reacting substantially equimolar amounts of the carbamoyl chloride (IV) and the amine (V) in the presence of an inert solvent at a temperature of 0° to 150° C. Preferably the reaction is conducted in the presence of an acid acceptor, e.g., an organic amine such as a trialkylamine or a pyridine compound. The urea product (VI) is isolated by conventional procedures such as extraction, filtration, chromatography, etc.

EXAMPLE I — Preparation of N-trichloromethylthio-N-methyl carbamoyl chloride

A solution of 37.2 g (0.2 mol) trichloromethylsulfenyl chloride in 100 ml of benzene was added dropwise to a solution of 6.2 g (0.2 mol) of methylamine and 20.2 g (0.2 mol) of triethylamine in 100 ml of benzene at a temperature of 5°–8° C. After the addition was completed, the reaction mixture was stirred for 10 minutes and then filtered to remove the triethylamine hydrochloride salt produced.

Into the resulting N-trichloromethylthio-N-methylamine filtrate solution was bubbled 19.8 g (0.2 mol) of phosgene at a temperature of 4°–8° C. The reaction mixture was stirred for 20 minutes, stored at about 0° C for 16 hours, and filtered. The filtrate was evaporated under reduced pressure to give 39.9 g of the N-trichloromethylthio-N-methylcarbamoyl chloride product. Elemental analysis for $C_3Cl_4NOS$ showed: %S, calc. 13.15, found 14.15; %Cl, calc. 58.6, found 54.45.

N-trichloromethylthio-N-methylcarbamoyl chloride, prepared by a similar procedure, had a boiling range of 62°–63° C at 0.15 mm Hg.

EXAMPLE II — Preparation of 2,3-dihydro-2,2-dimethyl-7-furanyl carbamate derivative of N-trichloromethylthio-N-methyl carbamoyl chloride A 7.16-g sample of sodium hydride oil dispersion (50% NaH, 0.149 mol NaH) was added in small portions to a solution of 24.5 g (0.149 mol) of 2,3-dihydro-2,2-dimethyl-7-benzofuranol in 150 ml benzene. After the addition was completed, the reaction mixture was warmed to 45° C and stirred until hydrogen evolution ceased. The reaction mixture was cooled and 39.9 g of N-trichloromethylthio-N-methylcarbamoyl chloride (prepared as in Example I) in 40 ml of benzene was added dropwise at about 25° C. After the carbamoyl chloride was added, the reaction mixture was stirred at about 25° C for 3 to 4 hours and stored at about 25° C for about 16 hours. The reaction mixture was then washed with water. The water washes were extracted with benzene. The combined organic solutions were dried over magnesium sulfate and evaporated under reduced pressure to give the crude product. The crude product was purified by chromatography (benzene eluent) and crystallization from hexane to give 21.5 g of N-methyl-N-trichloromethylthio-2,3-dihydro-2,2-dimethyl-7-benzofuranyl carbamate, m.p. 88.5°–89.5° C. The carbamate has insecticidal aceivity, as disclosed in U.S. Pat. No. 3,847,951.

EXAMPLE III — Preparation of N-trichloromethylthio-N-propyl carbamoyl cloride A solution of 59.1 g (1 mol) N-propylamine and 101.2 g (1 mol) triethylamine in 200 ml acetonitrile was added dropwise to a solution of 185.9 g (1 mol) of trichloromethylsulfenyl chloride in 1 liter of acetonitrile at about 0°–5° C over a 1-hour period. Into the reaction mixture was then added 98.9 g (1 mol) phosgene over a 1-hour period. The reaction was stirred at about 25° C for about 16 hours. The solvent was evaporated under reduced pressure, and the residue was extracted with hexane. The hexane extracts were evaporated under reduced pressure to give a dark oil. The oil was distilled through a short column to give 22 g of the carbamoyl chloride product, b.p. 71°–81° C at 0.75 mm Hg.

EXAMPLE IV — Preparation of N-1,1,2,2-tetrachloroethylthio-N-methyl carbamoyl chloride A solution of 13.3 g (0.43 mol) methylamine and 43.4 g (0.43 mol) triethylamine in 100 ml acetonitrile was added dropwise to a solution of 100.0 g (0.43 mol) 1,1,2,2-tetrachloroethylsulfenyl chloride in 500 ml acetonitrile at about 0°–5° C over a 1-hour period. The reaction was stirred at about 25° C for 1 hour. The solvent was evaporated under reduced pressure and the residue extracted with hexane. The hexane extracts were evaporated under reduced pressure to give the product as an oil.

EXAMPLE V — Preparation of N-carbomethoxy-dichloromethylthio-N-methyl carbamoyl chloride A 70-g sample of chlorine was bubbled into 106.1 g of methyl thioglycolate at 0° C. A 1.5-g sample of sulfuric acid was then added. An additional 167 g of chlorine was added at 0°–5° C over about 80 minutes. After the addition was completed, the reaction mixture was allowed to warm up to about 25° C. Distillation through a short column gave 129.3 g of carbomethoxydichloromethylsulphenyl chloride, b.p. 50° C at 0.2 mm Hg.

A solution of 105 g of carbomethoxydichloromethylsulfenyl chloride (prepared above) in 600 ml acetonitrile was cooled in an ice bath while a mixture of 15.5 g methylamine and 50.5 g triethylamine in 100 ml acetonitrile was added over a 1-hour peroid. Amine hydrochloride precipitated during the addition. The reaction was stirred 1 hour at about 25° C. The mixture was cooled in an ice bath and an additional 25 g triethylamine ws then added. The reaction mixture was then stirred at about 25° C for 4 hours and allowed to stand for about 17 hours at 25° C. The solvent was evaporated under reduced pressure and the residue was extracted with hexane followed by benzene. The hexane and benzene extractants were evaporated under reduced pressure to give the product as an oil.

EXAMPLE VI — Preparation of 1-carbomethoxydichloromethylthio-1-methyl-3-phenyl urea A solution of 15 g N-carbomethoxydichloromethylthio-N-methyl carbamoyl chloride (prepared as described in Example V) in 150 of acetonitrile was cooled in an acetone-ice bath while 10.5 g aniline in 20 ml acetonitrile was added dropwise over 1 hour. The solvent was extracted with benzene. The benzene extracts were evaporated and the residue was chromatographed on silica gel (benzene eluent) to give the product as an oil which solidified on standing. Recrystallization from hexane gave a product which melted at 77°–78° C. Elemental analysis for the product is tabulated in Table I.

Compound Nos. 2–5 of Table I were prepared by a procedure similar to that of Example VI.

TABLE I

| Compound No. | Compound | Melting Point, °C | Elemental Analysis | | | |
|---|---|---|---|---|---|---|
| | | | Sulfur | | Chlorine | |
| | | | Calc. | Found | Calc. | Found |
| 1 | N-methyl-N-carbomethoxydichloromethylthio-N'-phenyl urea | 77–78 | 9.9 | 10.0 | 22.0 | 22.0 |
| 2 | N-methyl-N-1,1,2,2-tetrachloroethylthio-N'-o-fluorophenyl urea | 72 | 8.8 | 8.8 | 38.8 | 37.1 |
| 3 | N-methyl-N-1,1,2,2-tetrachloroethylthio-N'-m-trifluoromethylphenyl urea | Oil | 7.8 | 7.8 | 35.0 | 34.3 |
| 4 | N-methyl-N-trichloromethylthio-N'-p-chlorophenyl urea | 98–100 | 9.6 | 9.1 | 42.5 | 40.0 |
| 5 | N-methyl-N-trichloromethylthio-N'-o-fluorophenyl urea | 66–67 | 10.1 | 10.0 | 33.5 | 33.5 |

UTILITY

The urea compounds tabulated in Table I are, in general, herbicidal in both pre- and post-emergent applications. For pre-emergent control of undesirable vegetation, the herbicidal compounds will be applied in herbicidally effective amounts to the locus or growth medium of the vegetation, e.g., soil infested with seeds and/or seedlings of such vegetation. Such application will inhibit the growth of or kill the seeds, germinating seeds and seedlings. For post-emergent applications, the herbicidal compounds will be applied directly to the foliage and other plant parts. Generally, the herbicidal compounds are effective against weed grasses as well as broadleaved weeds. Some may be selective with respect to the type of application and/or type of weed.

The urea compounds can be used alone as herbicides. However, it is generally desirable to apply the compounds in herbicidal compositions comprising one or more of the herbicidal compounds intimately admixed with a biologically inert carrier. The carrier may be a liquid diluent or a solid, e.g., in the form of dust powder or granules. In the herbicidal composition, the active herbicidal compounds can be from about 0.01 to 95% by weight of the entire composition.

Suitable liquid diluent carriers include water and organic solvents, e.g., hydrocarbons such as benzene, toluene, kerosene, diesel oil, fuel oil, and petroleum naphtha. Suitable solid carriers are natural clays such as kaolinite, atalpulgite, and montmorillonite. In addition, talcs, pyrophillite, diatomaceous silica, synthetic fine silicas, calcium aluminosilicate and tricalcium phosphate are suitable carriers. Organic materials such as walnut-shell flour, cottonseed hulls, wheat flour, wood flour or redwood-bark flour may also be used as solid carriers.

The herbicidal composition will also usually contain a minor amount of a surface-active agent. Such surface agents are those commonly known as wetting agents, dispersing agents and emulsifying agents, and can be anionic, cationic or nonionic in character. The herbicidal compositions may also contain other pesticides, adjuvants, stabilizers, conditioners, fillers, and the like.

The amount of herbicidal compound or composition administered will vary with the particular plant part or plant growth medium which is to be contacted, the general location of application — i.e., sheltered areas such as greenhouses, as compared to exposed areas such as fields — as well as the desired type of control. Generally for both pre- and post-emergent control, the herbicidal compounds of the invention are applied at rates of 0.2 to 60 kg/ha, and the preferred rate is in the range 0.5 to 40 kg/ha.

Pre- and post-emergent herbicidal tests on the urea compounds were made using the following methods:

Pre-Emergent Test

An acetone solution of the test compound was prepared by mixing 750 mg of the compound, 220 mg of a nonionic surfactant and 25 ml of acetone. This solution was added to approximately 125 ml of water containing 156 mg of surfactant.

Seeds of the test vegetation were planted in a pot of soil and the test solution was sprayed uniformly onto the soil surface at a dose of 33 mcg/cm$^2$. The pot was watered and placed in a greenhouse. The pot was watered intermittently and was observed for seedling emergence, health of emerging seedlings, etc., for a 3-week period. At the end of this period, the herbicidal effectiveness of the compound was rated based on the physioligical observations. A 0-to-100 scale was used, 0 representing no phytotoxicity, 100 representing complete kill. The results of these tests appear in Table II.

Post-Emergent Test

The test compound was formulated in the same manner as described above for the pre-emergent test. The concentration of the test compound in this formulation was 5000 ppm. This formulation was uniformly sprayed on 2 similar pots of 24-day-old plants (approximately 15 to 25 plants per pot) at a dose of 33 mcg/cm$^2$. After the plants had dried, they were placed in a greenhouse and then watered intermittently at their bases, as needed. The plants were observed periodically for phytotoxic effects and physiological and morphological responses to the treatment. After 3 weeks, the herbicidal effectiveness of the compound was rated based on these observations. A 0-to-100 scale was used, 0 representing no phytotoxicity and 100 representing complete kill. The results of these tests appear in Table II.

TABLE II

| Compound No. | Herbicidal Effctiveness Pre-Post | | | | | |
|---|---|---|---|---|---|---|
| | O | W | C | M | P | L |
| 1 | 100/30 | 100/15 | 100/10 | 100/100 | 100/55 | 100/90 |
| 2 | 100/100 | 100/100 | 100/100 | 100/100 | 100/100 | 100/100 |
| 3 | 70/100 | 65/100 | 100/80 | 100/100 | 100/100 | 100/100 |
| 4 | 100/95 | 100/100 | 100/ | 100/100 | 100/100 | 100/100 |
| 5 | 100/100 | 100/100 | 100/100 | 100/100 | 100/100 | 100/100 |

O=Wild Oats (*Avena fatua*)
W=Watergrass (*Echinochloa crusgalli*)
C=Crabgrass (*Digitaria sanguinalis*)
M=Mustard (*Brassica Arvensis*)
P=Pigweed (*Amaranthus retroflexus*)
L=Lambsquarter (*Chenopodium album*)

What is claimed is:
1. A compound of the formula
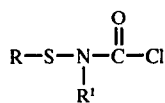
where R is haloalkyl having 1 to 3 carbon atoms, having 1 to 5 chlorine or bromine atoms and having one carboalkoxy having 2 to 6 carbon atoms and $R^1$ is alkyl having 1 to 6 carbon atoms.
2. N-carbomethoxydichloromethylthio-N-methyl carbamoyl chloride, according to claim 1.